United States Patent
Indo et al.

(10) Patent No.: US 9,441,481 B2
(45) Date of Patent: Sep. 13, 2016

(54) METHOD AND APPARATUS FOR IDENTIFYING FLUID ATTRIBUTES

(71) Applicant: Schlumberger Technology Corporation, Sugar Land, TX (US)

(72) Inventors: Kentaro Indo, Sugar Land, TX (US); Julian Pop, Houston, TX (US); Kai Hsu, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 41 days.

(21) Appl. No.: 14/408,550

(22) PCT Filed: Mar. 13, 2013

(86) PCT No.: PCT/US2013/030637
§ 371 (c)(1),
(2) Date: Dec. 16, 2014

(87) PCT Pub. No.: WO2014/003840
PCT Pub. Date: Jan. 3, 2014

(65) Prior Publication Data
US 2015/0204189 A1 Jul. 23, 2015

Related U.S. Application Data

(60) Provisional application No. 61/666,593, filed on Jun. 29, 2012.

(51) Int. Cl.
*E21B 49/08* (2006.01)
*G01N 21/31* (2006.01)
(Continued)

(52) U.S. Cl.
CPC .......... *E21B 49/088* (2013.01); *E21B 47/102* (2013.01); *G01N 21/359* (2013.01); *G01V 8/10* (2013.01); *G01N 21/31* (2013.01); *G01V 8/00* (2013.01)

(58) Field of Classification Search
None
See application file for complete search history.

(56) References Cited

U.S. PATENT DOCUMENTS 3,496,350 A * 2/1970 Bray ................. G01V 9/007
250/254
3,896,312 A * 7/1975 Brown ............... G01N 21/3577
250/343

(Continued)

FOREIGN PATENT DOCUMENTS

| WO | 9900666 A1 | 1/1999 |
|---|---|---|
| WO | 2009055200 A2 | 4/2009 |
| WO | 2014003840 A1 | 1/2014 |

OTHER PUBLICATIONS

European Search Report issued in related EP application 13810851.9 on Apr. 14, 2016, 4 pages.
(Continued)

*Primary Examiner* — Tri Ton
*Assistant Examiner* — Jarreas C Underwood
(74) *Attorney, Agent, or Firm* — David G. Matthews; Cathy Hewitt

(57) ABSTRACT

A method for identifying the type of a sampled formation fluid, such as a hydrocarbon, is provided. In one embodiment, the method includes measuring absorbance by a sample of a formation fluid at multiple wavelengths of electromagnetic radiation with a spectrometer. The method also includes distinguishing between multiple fluid types to identify a fluid type of the sample most likely to match an actual fluid type of the sample based on the measured absorbance at two or more wavelengths of the multiple wavelengths. Additional systems, devices, and methods are also disclosed.

15 Claims, 10 Drawing Sheets

(51) Int. Cl.
*G01V 8/00* (2006.01)
*E21B 47/10* (2012.01)
*G01N 21/359* (2014.01)
*G01V 8/10* (2006.01)

(56) References Cited

U.S. PATENT DOCUMENTS

| | | | | |
|---|---|---|---|---|
| 4,492,863 | A * | 1/1985 | Smith, Jr. | G01V 5/06 250/256 |
| 4,620,284 | A | 10/1986 | Schnell et al. | |
| 5,317,156 | A * | 5/1994 | Cooper | G01N 21/39 250/339.13 |
| 6,184,980 | B1 * | 2/2001 | Brown | G01J 3/42 356/300 |
| 6,388,251 | B1 * | 5/2002 | Papanyan | E21B 47/102 250/256 |
| 6,467,340 | B1 * | 10/2002 | Gallagher | E21B 37/06 166/250.05 |
| 6,888,127 | B2 * | 5/2005 | Jones | G01N 21/31 250/269.1 |
| 6,891,606 | B2 * | 5/2005 | Smith | E21B 37/06 356/128 |
| 7,236,811 | B2 * | 6/2007 | Schmitt | A61B 5/0059 600/310 |
| 7,362,422 | B2 | 4/2008 | DiFoggio et al. | |
| 7,423,258 | B2 * | 9/2008 | DiFoggio | G01J 3/02 250/269.1 |
| 7,601,950 | B2 * | 10/2009 | Kischkat | E21B 49/08 250/269.1 |
| 7,920,970 | B2 | 4/2011 | Zuo et al. | |
| 7,937,223 | B2 | 5/2011 | Ciglenec et al. | |
| 8,058,071 | B2 | 11/2011 | Jiang et al. | |
| 8,068,226 | B2 * | 11/2011 | Csutak | G01N 21/51 356/432 |
| 2004/0069942 | A1 | 4/2004 | Fujisawa et al. | |
| 2007/0035737 | A1 * | 2/2007 | Andrews | G01N 21/3577 356/436 |
| 2007/0120051 | A1 | 5/2007 | DiFoggio et al. | |
| 2009/0296086 | A1 * | 12/2009 | Appel | G01N 21/3586 356/326 |
| 2010/0065793 | A1 * | 3/2010 | Hart | A61B 1/043 252/582 |

OTHER PUBLICATIONS

International Search Report for International Application No. PCTUS2013030637 dated Jun. 7, 2013.
European Examination Report issued in related EP application 13810851.9 on Apr. 29, 2016, 5 pages.

* cited by examiner

METHOD AND APPARATUS FOR IDENTIFYING FLUID ATTRIBUTES

BACKGROUND

Wells are generally drilled into subsurface rocks to access fluids, such as hydrocarbons, stored in subterranean formations. The formations penetrated by a well can be evaluated for various purposes, including for identifying hydrocarbon reservoirs within the formations. During drilling operations, one or more drilling tools in a drill string may be used to test or sample the formations. Following removal of the drill string, a wireline tool may also be run into the well to test or sample the formations. These drilling tools and wireline tools, as well as other wellbore tools conveyed on coiled tubing, drill pipe, casing or other means of conveyance, are also referred to herein as "downhole tools." Certain downhole tools may include two or more integrated collar assemblies, each for performing a separate function, and a downhole tool may be employed alone or in combination with other downhole tools in a downhole tool string.

Formation evaluation may involve drawing fluid from the formation into a downhole tool. In some instances, the fluid drawn from the formation is retained within the downhole tool for later testing outside of the well. In other instances, downhole fluid analysis may be used to test the fluid while it remains in the well. Such analysis can be used to provide information on certain fluid properties in real time without the delay associated with returning fluid samples to the surface.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

The present disclosure relates to downhole fluid analysis, and more particularly to downhole fluid analysis using optical spectrometry, such as near-infrared optical spectrometry. The techniques described herein may be employed to identify a characteristic, such as a fluid type, of a formation fluid drawn into a downhole tool. For example, the techniques described herein may be employed to determine whether the fluid type is oil, gas condensate, wet gas, or dry gas, among others. According to certain embodiments, optical spectrometry may be employed to determine the optical density of the fluid at two or more wavelengths. The optical density of the fluid may then be used to calculate an optical density ratio, which in turn may be employed to identify the fluid type, as described further below. The downhole fluid analysis techniques may be performed downhole and in certain embodiments, in substantially real time. For example, in certain embodiments, the downhole tool may include a fluid analysis module. Further, the downhole fluid analysis techniques described herein may be performed by one or more controllers or processors, which may use algorithms, executable code, or lookup tables stored in memory to determine the fluid type or otherwise characterize a sampled fluid.

Various refinements of the features noted above may exist in relation to various aspects of the present embodiments. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not require any particular orientation of the components.

Figure 1:
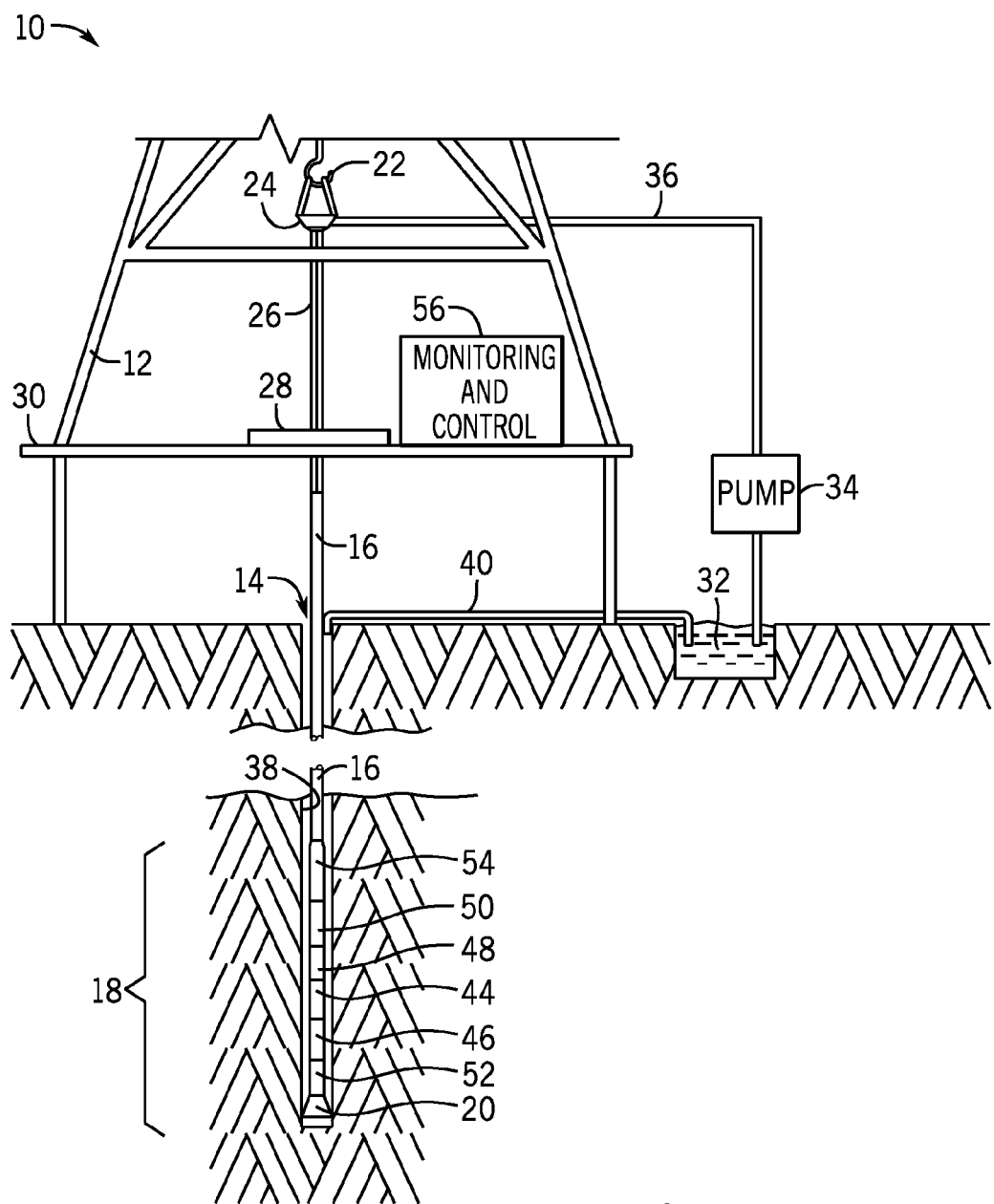
FIG. 1 generally depicts a drilling system having a fluid sampling tool in a drill string in accordance with one embodiment of the present disclosure.

Turning now to the drawings, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 includes a drilling rig 12 positioned over a well 14. Although depicted as an onshore drilling system 10, it is noted that the drilling system could instead be an offshore drilling system. The drilling rig 12 supports a drill string 16 that includes a bottomhole assembly 18 having a drill bit 20. The drilling rig 12 can rotate the drill string 16 (and its drill bit 20) to drill the well 14.

The drill string 16 is suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In the presently illustrated embodiment, a rotary table 28 on a drill floor 30 of the drilling rig 12 is constructed to grip and turn the kelly 26 to drive rotation of the drill string 16 to drill the well 14. But in other embodiments a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 is circulated through the well 14 by a pump 34. The drilling fluid 32 is pumped from a mud pit (or some other reservoir, such as a mud tank) into the drill string 16 through a supply conduit 36, the swivel 24, and the kelly 26. The drilling fluid 32 exits near the bottom of the drill string 16 (e.g., at the drill bit 20) and returns to the surface through the annulus 38 between the wellbore and the drill string 16. A return conduit 40 transmits the returning drilling fluid 32 away from the well 14. In some embodiments, the returning drilling fluid 32 is cleansed (e.g., via one or more shale shakers, desanders, or desilters) and reused in the well 14.

In addition to the drill bit 20, the bottomhole assembly 18 also includes various instruments that measure information of interest within the well 14. For example, as depicted in FIG. 1, the bottomhole assembly 18 includes a logging-while-drilling (LWD) module 44 and a measurement-while-drilling (MWD) module 46. Both modules include sensors, housed in drill collars, that collect data and enable the creation of measurement logs in real-time during a drilling operation. The modules could also include memory devices for storing the measured data. The LWD module 44 includes sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 includes sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. And as discussed in greater detail below, one or more of the modules 44, 46, and 48 is or includes a fluid sampling tool configured to obtain a sample of a fluid from a subterranean formation and perform downhole fluid analysis to identify a physical attribute of the sampled formation fluid, such as fluid type.

The bottomhole assembly 18 can also include other modules. As depicted in FIG. 1 by way of example, such other modules include a power module 50, a steering module 52, and a communication module 54. In one embodiment, the power module 50 includes a generator (such as a turbine) driven by flow of drilling mud through the drill string 16. But in other embodiments the power module 50 could also or instead include other forms of power storage or generation, such as batteries or fuel cells. The steering module 52 may include a rotary-steerable system that facilitates directional drilling of the well 14. The communication module 54 enables communication of data (e.g., data collected by the LWD module 44 and the MWD module 46) between the bottomhole assembly 18 and the surface. In one embodiment, the communication module 54 communicates via mud pulse telemetry, in which the communication module 54 uses the drilling fluid 32 in the drill string as a propagation medium for a pressure wave encoding the data to be transmitted.

The drilling system 10 also includes a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
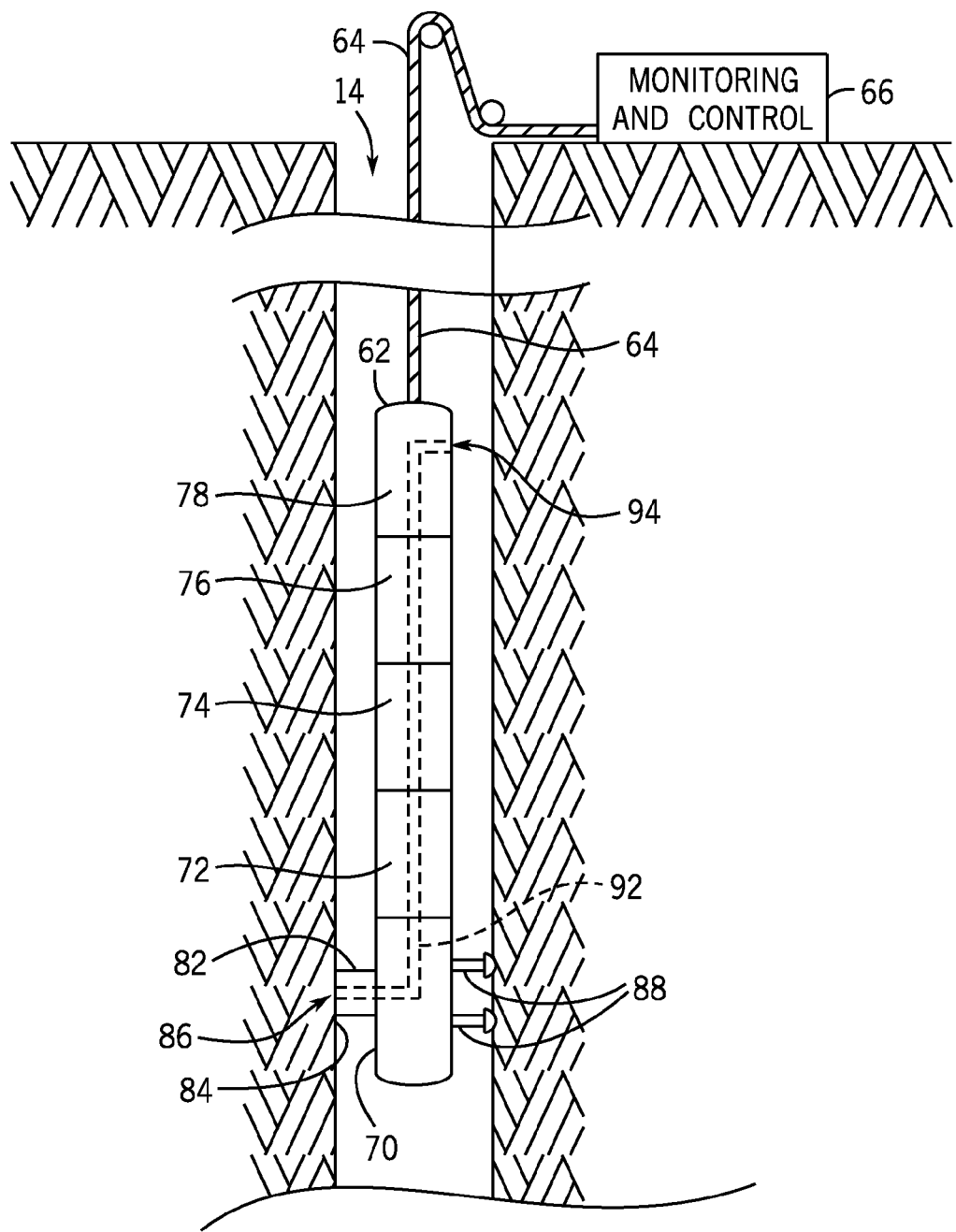
FIG. 2 generally depicts a fluid sampling tool deployed within a well on a wireline in accordance with one embodiment.

Another example of using a downhole tool for formation testing within the well 14 is depicted in FIG. 2. In this embodiment, a fluid sampling tool 62 is suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 controls movement of the fluid sampling tool 62 within the well 14 and receives data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) is incorporated into or as one or more modules of the bottom-hole assembly 18, such as the LWD module 44 or the additional module 48.

The fluid sampling tool 62 can take various forms. While it is depicted in FIG. 2 as having a body including a probe module 70, a fluid analysis module 72, a pump module 74, a power module 76, and a fluid storage module 78, the fluid sampling tool 62 may include different modules in other embodiments. The probe module 70 includes a probe 82 that may be extended (e.g., hydraulically driven) and pressed into engagement against a wall 84 of the well 14 to draw fluid from a formation into the fluid sampling tool 62 through an intake 86. As depicted, the probe module 70 also includes one or more setting pistons 88 that may be extended outwardly to engage the wall 84 and push the end face of the probe 82 against another portion of the wall 84. In some embodiments, the probe 82 includes a sealing element or packer that isolates the intake 86 from the rest of the wellbore. But in other embodiments the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 draws the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The fluid analysis module 72 includes one or more sensors for measuring properties of the sampled formation fluid, such as the optical properties discussed in greater detail below, and the power module 76 provides power to electronic components of the fluid sampling tool 62.

The drilling and wireline environments depicted in FIGS. 1 and 2 are examples of environments in which a fluid sampling tool may be used to facilitate analysis of a downhole fluid. But the presently disclosed techniques could be implemented in other environments as well. For instance, the fluid sampling tool 62 may be deployed in other manners, such as by a slickline, coiled tubing, or a pipe string.

Figure 3:
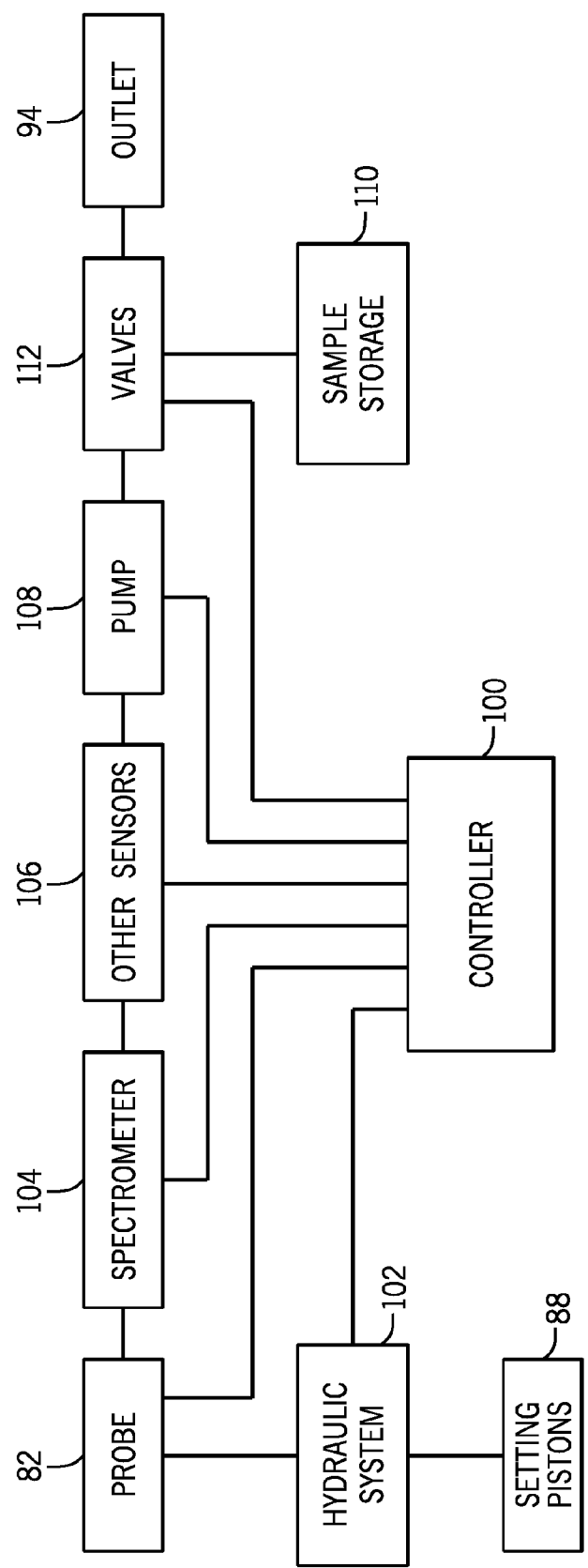
FIG. 3 is a block diagram of components of a fluid sampling tool operated by a controller in accordance with one embodiment.

Additional details as to the construction and operation of the fluid sampling tool 62 may be better understood through reference to FIG. 3. As shown in this figure, various components for carrying out functions of the fluid sampling tool 62 are connected to a controller 100. The various components include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting it through the outlet 94.

In operation, the hydraulic system 102 extends the probe 82 and the setting pistons 88 to facilitate sampling of a formation fluid through the wall 84 of the well 14. It also retracts the probe 82 and the setting pistons 88 to facilitate subsequent movement of the fluid sampling tool 62 within the well. The spectrometer 104, which can be positioned within the fluid analysis module 72, collects data about optical properties of the sampled formation fluid. As discussed in greater detail below, such measured optical properties may include optical densities of the sampled formation fluid at different wavelengths of electromagnetic radiation. Other sensors 106 can be provided in the fluid sampling tool 62 (e.g., as part of the probe module 70 or the fluid analysis module 72) to take additional measurements related to the sampled fluid. In various embodiments, these additional measurements could include pressure and temperature, density, viscosity, electrical resistivity, saturation pressure, and fluorescence, to name several examples. Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 facilitates operation of the fluid sampling tool 62 by controlling various components. Specifically, the controller 100 directs operation (e.g., by sending command signals) of the hydraulic system 102 to extend and retract the probe 82 and the setting pistons 88 and of the pump 108 to draw formation fluid samples into and through the fluid sampling tool. The controller 100 also receives data from the spectrometer 104 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 also operates the valves 112 to divert sampled fluids from the flowline 92 into the storage devices 110.

Figure 4:
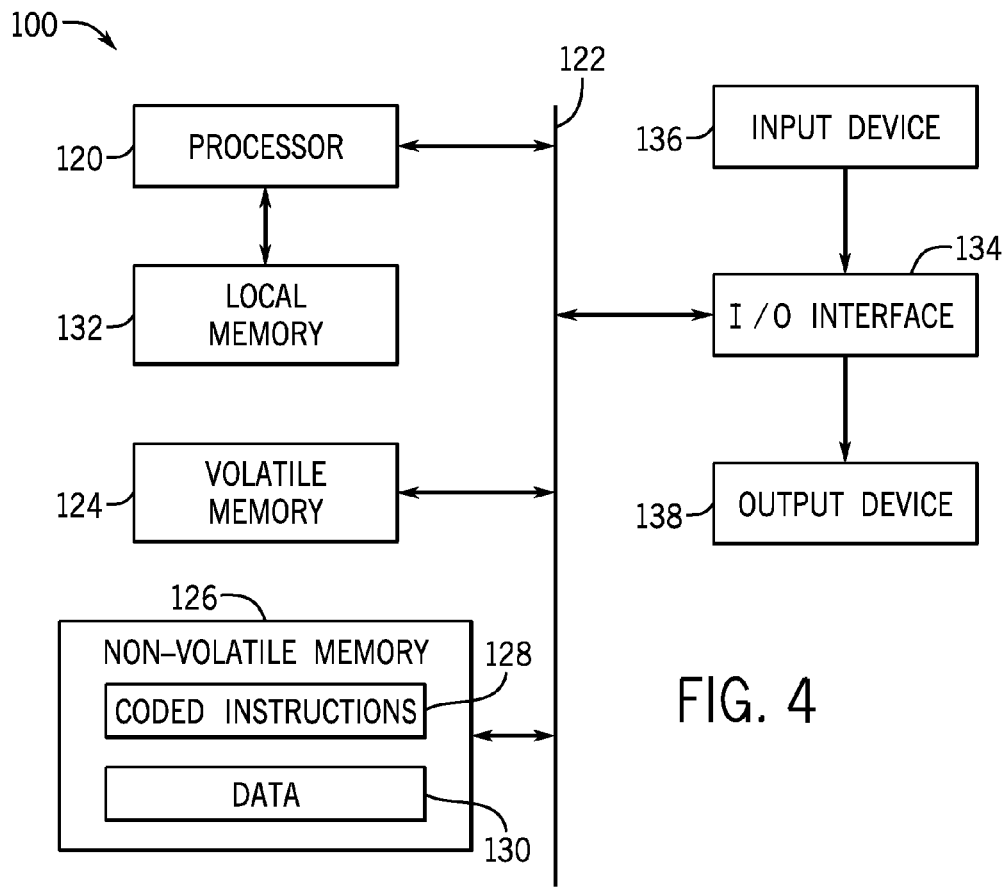
FIG. 4 is a block diagram of components in one example of the controller illustrated in FIG. 3.

The controller 100 in some embodiments is a processor-based system, an example of which is provided in FIG. 4. In this depicted embodiment, the controller 100 includes at least one processor 120 connected, by a bus 122, to volatile memory 124 (e.g., random-access memory) and non-volatile memory 126 (e.g., flash memory and a read-only memory (ROM)). Coded application instructions 128 (e.g., software that may be executed by the processor 120 to enable the control and analysis functionality described herein) and data 130 are stored in the non-volatile memory 126. For example, the application instructions 128 can be stored in a ROM and the data can be stored in a flash memory. The instructions 128 and the data 130 may be also be loaded into the volatile memory 124 (or in a local memory 132 of the processor) as desired, such as to reduce latency and increase operating efficiency of the controller 100. An interface 134 of the controller 100 enables communication between the processor 120 and various input devices 136 and output devices 138. The interface 134 can include any suitable device that enables such communication, such as a modem or a serial port. In some embodiments, the input devices 136 include one or more sensing components of the fluid sampling tool 62 (e.g., the spectrometer 104) and the output devices 138 include displays, printers, and storage devices that allow output of data received or generated by the controller 100. The input devices 136 and the output devices 138 may be provided as part of the controller 100, although in other embodiments such devices may be separately provided.

The controller 100 can be provided as part of the monitoring and control systems 56 or 66 outside of a well 14 to enable downhole fluid analysis of samples obtained by the fluid sampling tool 62. In such embodiments, data collected by the fluid sampling tool 62 can be transmitted from the well 14 to the surface for analysis by the controller 100. But in some embodiments, the controller 100 is instead provided within a downhole tool in the well 14, such as within the fluid sampling tool 62 or in another component of the bottomhole assembly 18, to enable downhole fluid analysis to be performed within the well 14. Further, the controller 100 may be a distributed system with some components located in a downhole tool and others provided elsewhere (e.g., at the surface of the wellsite).

Whether provided within or outside the well 14, the controller 100 can receive data collected by the sensors within the fluid sampling tool 62 and process this data to determine one or more characteristics of the sampled fluid. Examples of such characteristics include fluid type, gas-to-oil ratio, carbon dioxide content, water content, and contamination. And as noted above, some of the data collected by the fluid sampling tool 62 relates to optical properties of a sampled fluid as measured by the spectrometer 104.

Figure 5:
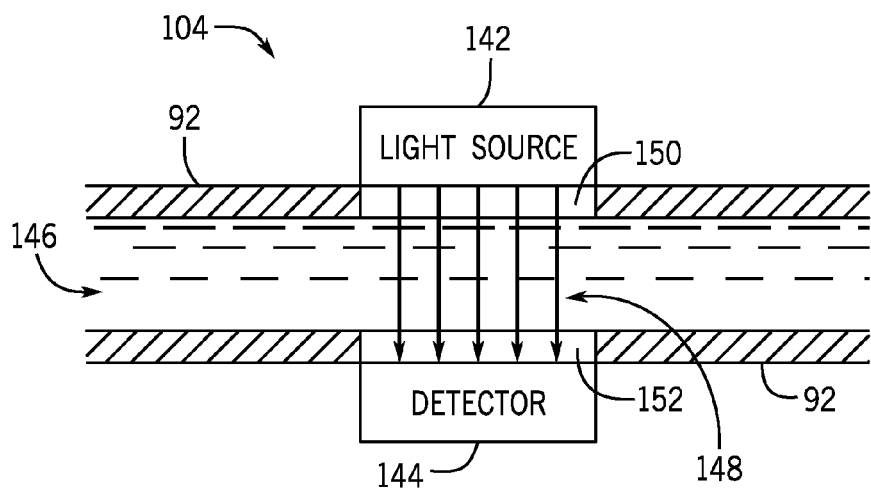
FIG. 5 generally depicts a spectrometer positioned about a flowline to enable measurement of an optical property of a fluid within the flowline in accordance with one embodiment.

To facilitate measurements, in some embodiments the spectrometer 104 may be arranged about the flowline 92 of the fluid sampling tool 62 in the manner generally depicted in FIG. 5. In this example, the spectrometer 104 includes an emitter of electromagnetic radiation, such as a light source 142, and a detector 144 disposed about the flowline 92 in the fluid sampling tool 62. The light source 142 can be any suitable light-emitting device, such as one or more light-emitting diodes or incandescent lamps. As used herein, the term "visible light" is intended to mean electromagnetic radiation within the visible spectrum, and the shorter term "light" is intended to include not just electromagnetic radiation within the visible spectrum, but also infrared and ultraviolet radiation.

In operation, a sampled formation fluid 146 within the flowline 92 is irradiated with electromagnetic radiation 148 (e.g., light) from the light source 142. The electromagnetic radiation 148 includes radiation of any desired wavelengths within the electromagnetic spectrum. In some embodiments, the electromagnetic radiation 148 has a continuous spectrum within one or both of the visible range and the near-infrared range of the electromagnetic spectrum, and the detector 144 filters or diffracts the received electromagnetic radiation 148. The detector 144 may include a plurality of detectors each assigned to separately measure light of a different wavelength. As depicted in FIG. 5, the flowline 92 includes windows 150 and 152 that isolate the light source 142 and the detector 144 from the sampled formation fluid 146 while still permitting the electromagnetic radiation 148 to be transmitted and measured. As will be appreciated, some portion of the electromagnetic radiation 148 is absorbed by the sampled fluid 146, and the extent of such absorption varies for different wavelengths. The optical density of the fluid 146 at one or more wavelengths may be determined based on data from the spectrometer 104 by comparing the amount of radiation emitted by the light source 142 and the amount of that radiation received at detector 144. It will be appreciated that the optical density (also referred to as the absorbance) of a fluid at a given wavelength is calculated as the base-ten logarithm of the ratio of electromagnetic radiation incident on the fluid to that transmitted through the fluid for the given wavelength.

The spectrometer 104 may include any suitable number of measurement channels for detecting different wavelengths, and may include a filter-array spectrometer or a grating spectrometer. For example, in some embodiments the spectrometer 104 is a filter-array absorption spectrometer having ten measurement channels. But in other embodiments, the spectrometer 104 may have sixteen channels or twenty channels, and may be provided as a filter-array spectrometer or a grating spectrometer.

Figure 6:
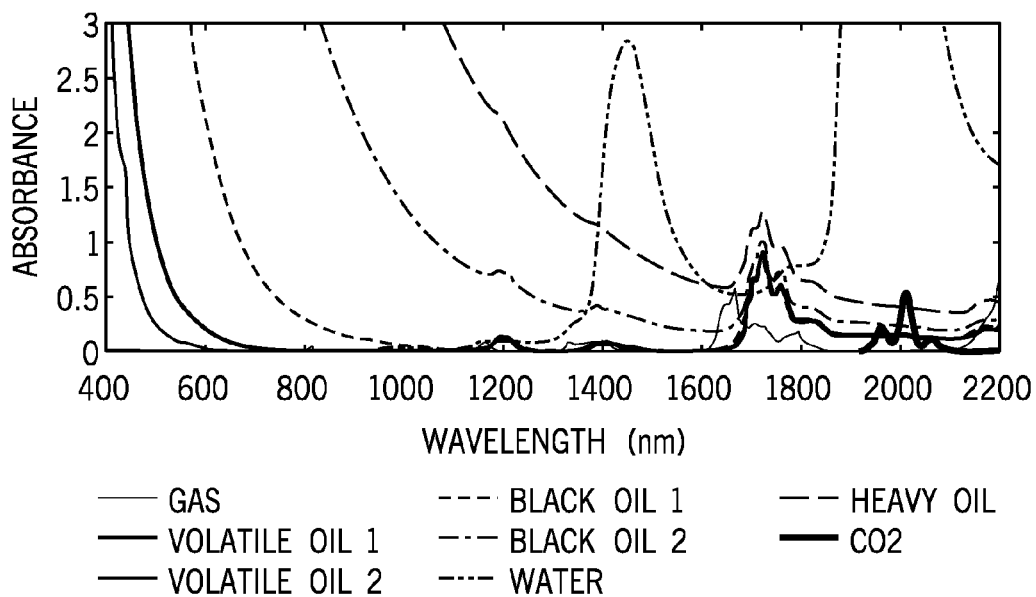
FIG. 6 is a graph representing optical spectra of examples of reservoir fluids for wavelengths in the visible and near-infrared ranges.
Figure 7:
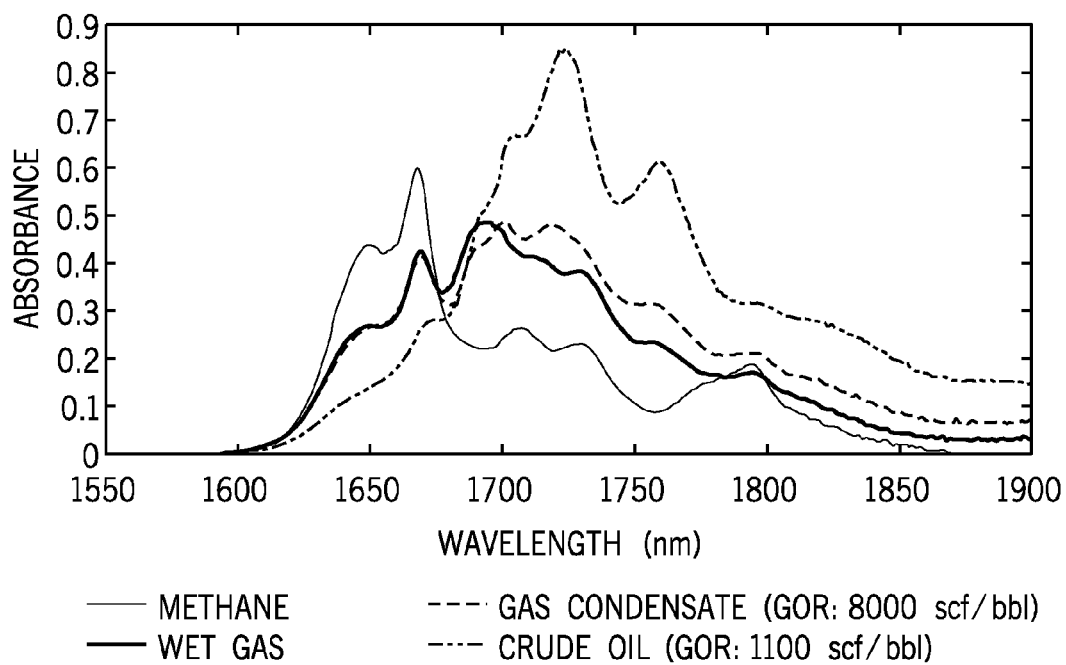
FIG. 7 is a graph representing optical spectra of examples of reservoir hydrocarbons for wavelengths within the near-infrared range.

By way of example, FIGS. 6 and 7 illustrate examples of absorbance spectra for certain reservoir fluids. More specifically, FIG. 6 depicts the absorbance spectra in the visible and near-infrared regions of the electromagnetic spectrum for methane (denoted "gas" in FIG. 6), water, carbon dioxide, and various crude oils (including volatile oils, black oils, and a heavy oil). Many crude oils, such as black and heavy oils, tend to have strong absorption in the ultraviolet and visible regions of the electromagnetic spectrum and have a "tail" in the 1000 nm to 1600 nm portion of the near-infrared region, which can be considered a signature of crude oils in their optical spectra. But volatile oils, similarly to dry gases, wet gases, and retrograde gases, have less absorption in the near-infrared region. Consequently, it can be more difficult to distinguish volatile oils from gases (dry, wet, or retrograde) based on optical spectra over the visible and near-infrared regions. The term "dry gas" is used herein to refer to a reservoir hydrocarbon gas that does not change phase (and therefore there is no liquid dropout) as it is brought to the surface. This is in contrast to a "wet gas," which occurs as a gas in the reservoir but produces a liquid condensate at the surface. Additionally, as used herein the term "retrograde gas," which is also referred to as "gas condensate," is a gas that exhibits a retrograde dew point in the reservoir and is a gas in the reservoir under original pressure but begins to form liquid condensate within the reservoir as pressure decreases with production and reverts back to a gaseous state under further reduction in pressure. Oils, including black oils and volatile oils, are liquid in the reservoir and when produced, provided the pressure at the wellbore is above the bubble-point pressure.

FIG. 7 shows an example of the optical spectra of a dry gas (methane), a wet gas, a retrograde gas (denoted "gas condensate" in this figure), and a crude oil measured in the wavelength range from 1550 nm to 1900 nm, which is a range where hydrocarbon vibrational absorption peaks are present. According to certain embodiments, the spectrometer 104 may allocate measurement channels to specific wavelengths within the range from 1550 nm to 1900 nm to enable determination of optical densities of the sampled fluid 146 at these specific wavelengths. These optical densities may then be compared in order to characterize some attribute of the sampled fluid 146, such as identifying the sampled fluid 146 by most likely type (e.g., as a dry gas, a wet gas, a retrograde gas, or an oil).

Figure 8:
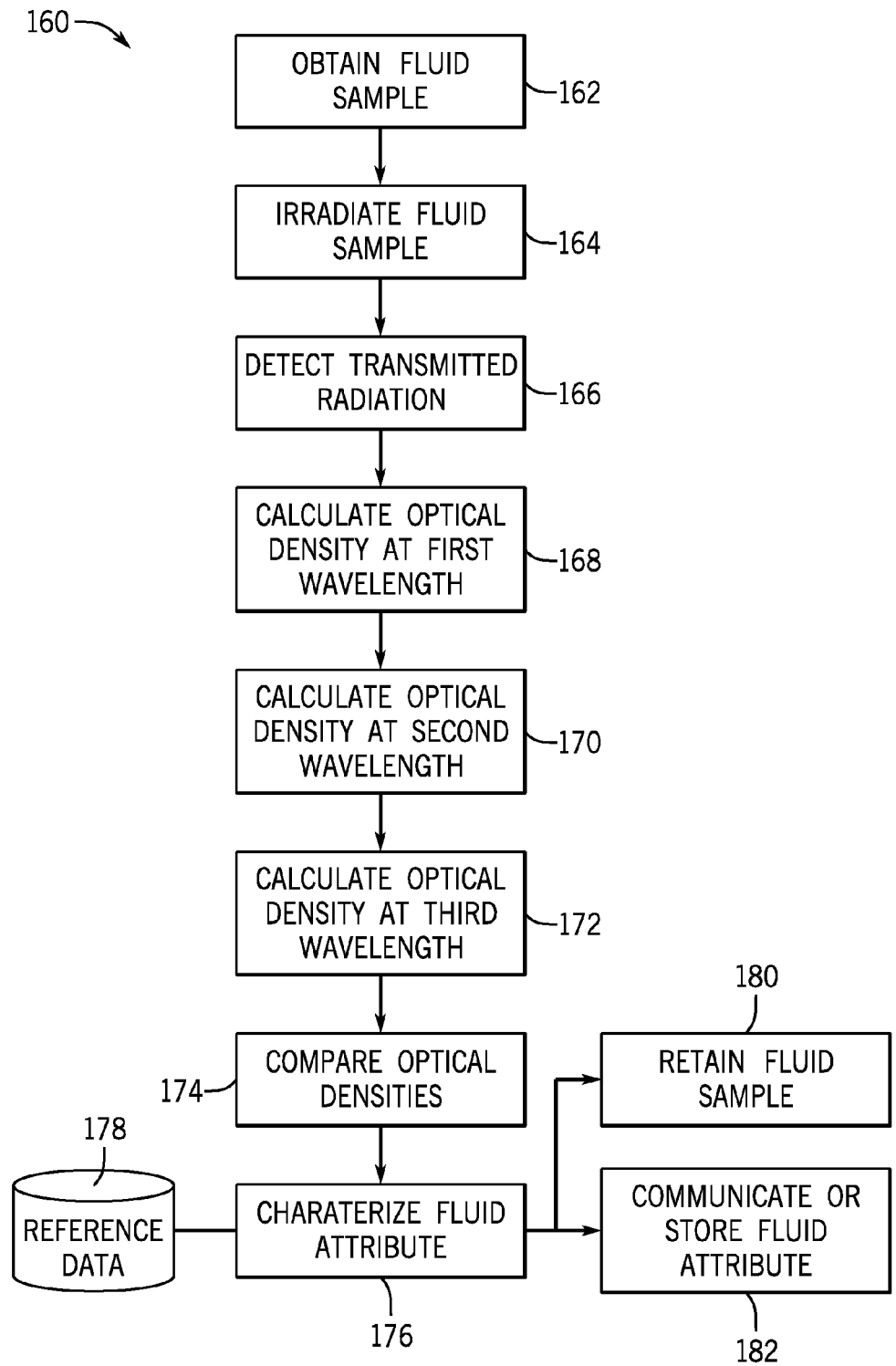
FIG. 8 is a flow chart for analyzing a fluid sample in accordance with one embodiment.

One example of a process for characterizing an attribute of a formation fluid is generally represented by flow chart 160 in FIG. 8. In this embodiment, a sample of a formation fluid is obtained (block 162). For instance, the formation fluid may be sampled by a downhole tool, such as with the fluid sampling tool 62 described above. The fluid sample is then irradiated (block 164) with electromagnetic radiation having multiple wavelengths and some amount of this radiation that is transmitted through the fluid is detected (block 166). The irradiation and detection of electromagnetic radiation can be performed by any of various suitable spectrometers 104. The electromagnetic radiation having multiple wavelengths can be polychromatic radiation from one light source, but in other instances the electromagnetic radiation having multiple wavelengths can be provided in other ways (e.g., with multiple light sources that each emit different monochromatic radiation, either simultaneously or at different times).

As represented by blocks 168 and 170, optical densities are then calculated for at least first and second wavelengths of the multiple wavelengths. The calculated optical densities may then be compared (block 174) to characterize (block 176) an attribute of the sampled fluid, such as a fluid type. The characterization of a fluid attribute may be facilitated by reference to a database of standardized reference data 178 (which may also be referred to as benchmark data) correlating fluid attributes to optical densities. In some embodiments, the comparison of the optical densities includes calculating a ratio of the optical densities and the standardized reference data 178 includes one or more look-up tables correlating optical density ratios of previously analyzed fluids (e.g., analyzed in a laboratory) with known attributes of those previously analyzed fluids. The calculated optical density ratio for the sampled fluid can be compared to the standardized data to determine one or more fluid attributes of the sampled fluid.

As discussed in greater detail below, the characterization of the fluid attribute may also be accompanied by a certainty level for that characterization. In cases where the characterization includes identifying a most likely fluid type, the certainty level may be a probability that the most likely fluid type is, in fact, the fluid type of the formation fluid sample. Probabilities that the actual fluid type is another of the fluid types from which the most likely fluid type was selected (that is, that a less likely fluid type matches the actual fluid type) may also be calculated for one or more of the other fluid types. In some instances in which there is a reasonable chance (the threshold of which may be set through programming) that either of two opposing characterizations is accurate, uncertainty as to the characterization may be expressed by returning both characterizations, with or without associated confidence levels.

Based on the characterization in block 176, the sampled fluid could be retained (block 180), if desired, and the characterized attribute could be communicated or stored for later use (block 182). The process generally represented by flow chart 160 can be carried out by any suitable devices or systems, such as the controller 100 (in which case the standardized reference data 178 may be stored in a memory device within controller 100) in connection with a downhole tool (e.g., LWD module 44 or additional module 48 of FIG. 1, or fluid sampling tool 62 of FIG. 2). And in some embodiments this process may be performed in real time without removing fluid samples from the well 14.

In the flow chart 160, an optical density for a third wavelength is also calculated (block 172). In some embodiments, this third optical density could be used as a spectral offset (e.g., to compensate for the impact of effects from scattering, window coating (which may attenuate the radiation from the spectrometer light source), and so forth). But in other embodiments, the optical densities at two wavelengths could be compared without calculating an optical density at a third wavelength.

By way of example, in some embodiments the spectrometer 104 allocates three measurement channels at 1600 nm, 1671 nm, and 1725 nm to enable calculation of optical densities of the fluid at these wavelengths. The optical spectra depicted in FIG. 7 demonstrate little absorbance at 1600 nm. Thus, this channel may be used for subtracting any spectral offset, as discussed above. As can be seen from FIG. 7, absorbance at 1671 nm is dominated by methane, although contributions from other fluid types are also present. At 1725 nm, liquid components at standard conditions have the highest absorbance, and most oils have the highest peak at 1725 nm. Conversely, gas and gas condensates (i.e., retrograde gases) generally contain a high fraction of methane and tend to have relatively high absorbance at 1671 nm compared to that at 1725 nm. Thus, in some embodiments the optical densities of these two channels are compared to facilitate characterization of fluid type or some other attribute. More specifically, the comparison of the optical densities may include determining an optical density ratio for the two wavelengths. In at least some embodiments, using such an optical density ratio may provide more accurate results than some other identification techniques, such as using color channels with their wavelengths in the "tail" portion (1000 nm to 1600 nm) of the near-infrared region.

The optical density ratio of two wavelength channels can be defined as follows:

$$\text{Optical density ratio} = \frac{\Omega_{\lambda 1} - \Omega_{baseline}}{\Omega_{\lambda 2} - \Omega_{baseline}} = \frac{\tilde{\Omega}_{\lambda 1}}{\tilde{\Omega}_{\lambda 2}}, \quad (1)$$

where $\Omega_{\lambda 1}$ and $\Omega_{\lambda 2}$ are optical densities at wavelengths $\lambda_1$ and $\lambda_2$, and $\Omega_{baseline}$ is an optical density calculated for an additional wavelength (considered to be a baseline channel). In the above example measuring optical densities at 1600 nm, 1671 nm, and 1725 nm, $\lambda_1$ and $\lambda_2$ are 1671 nm and 1725 nm, respectively, and 1600 nm is used as the baseline channel.

Figure 9:
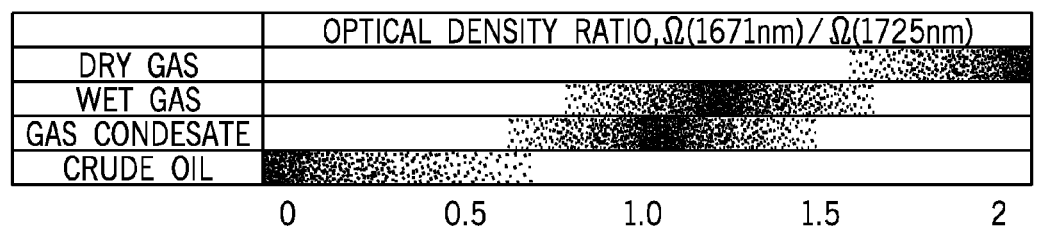
FIGS. 9 and 10 graphically depict correlations between certain fluid types and optical density ratios in accordance with one embodiment.

The optical density ratio and type of formation fluid can be empirically correlated, for example using an optical spectral database and laboratory Pressure-Volume-Temperature (PVT) analysis, as generally shown in FIG. 9. In this figure, distribution ranges of optical density ratios, derived from wavelengths of 1671 nm and 1725 nm (although ratios based on other wavelengths could be used in other embodiments), are shown for various fluid types identified through PVT analyses of reference fluids. Based on such correlations, a measured optical density ratio for a formation fluid sample of unknown type could be used to distinguish between various fluid types to identify a most likely fluid type (i.e., the fluid type most likely to match the actual fluid type). For instance, four unknown samples having calculated optical density ratios of 0.3, 0.7, 1.5, and 2.0 would most likely be, in order, a crude oil, a gas condensate, a wet gas, and a dry gas.

Figure 10:
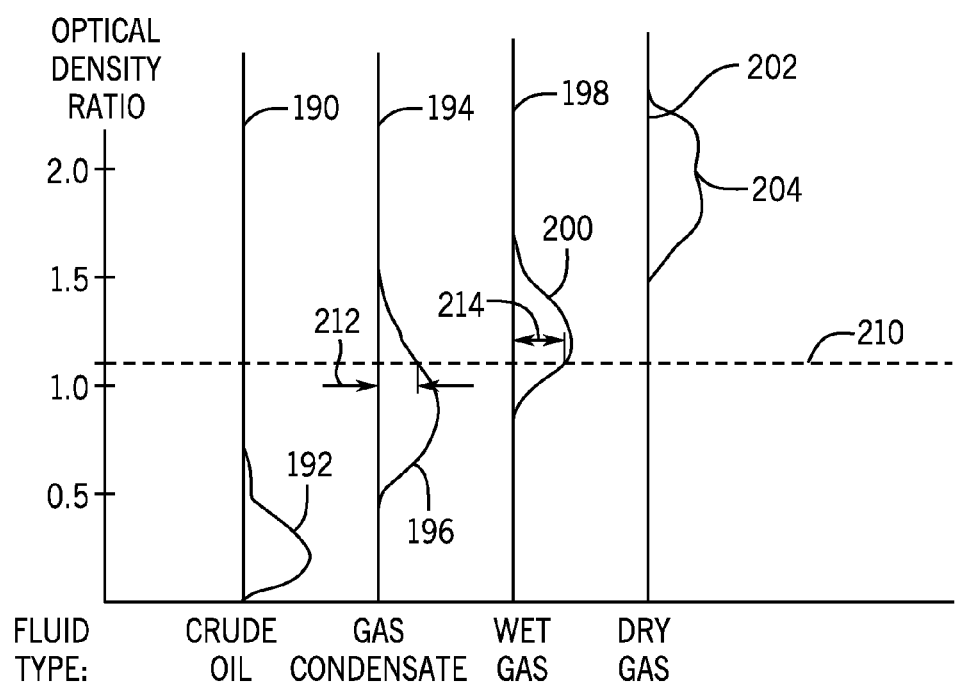

FIG. 10 similarly depicts correlations of optical density ratios to fluid types, but in a slightly different form in which optical density ratio distributions are depicted as curves with respect to axes for the fluid types in FIG. 9. These distributions may be representative of optical density ratios calculated based on any desired wavelengths, and are not representative of any particular ratio (such as the ratio of optical densities at 1671 nm and 1725 nm above). Axes 190, 194, 198, and 202 are provided in FIG. 10 for each of crude oil, gas condensate, wet gas, and dry gas. Curves 192, 196, 200, and 204 represent the observed distributions of optical density ratios for fluid of known types (which may have been determined through PVT analysis or in some other suitable manner).

As noted above, an optical density ratio may be calculated for a formation fluid sample of unknown type (e.g., a fluid sample within the fluid sampling tool 62 during analysis) and compared to reference data associating fluids with known types (from previously known and analyzed fluids) to optical density ratios measured from those fluids to characterize the fluid type of the presently analyzed formation fluid sample. And in some embodiments, the characterization of fluid type of an unknown sample may include determining probabilities that one or more of the possible fluid types are the actual fluid type of the unknown sample. For example, if the optical density ratio is calculated to be 1.1, as generally represented by dashed line 210, the magnitudes of the curves 196 and 200 at line 210 may be used to calculate probabilities that the unknown fluid is a gas condensate or a wet gas. Specifically, the extent of deviation of curves 196 and 200 from axes 194 and 198, represented here as distances 212 and 214, may be quantified. On this basis, the magnitude of each distance 212 and 214 may be divided by the sum of the distances 212 and 214 to calculate the probabilities that the unknown fluid is a gas condensate or a wet gas, respectively. Although FIGS. 9 and 10 refer to four types of fluids—dry gas, wet gas, gas condensate, and crude oil—it should be appreciated that other or additional types of fluids could also be correlated with optical properties and serve as a basis for identifying an unknown fluid as being one of such other or additional fluid types. Examples of such fluid types include black oils, heavy oils, volatile oils, paraffin-based crude oils, asphalt-based crude oils, sweet crudes, and sour crudes.

It is again noted that other wavelengths may also or instead be used for constructing correlations between optical density ratio and the fluid type. For instance, methane has relatively high absorbance at 1650 nm and crude oil has a strong absorbance at 1760 nm as well. Accordingly, in other embodiments, the spectrometer 104 may be used to measure transmitted radiation of other wavelengths to facilitate calculation of optical densities (and in some instances optical density ratios) based on those other wavelengths.

Figure 11:
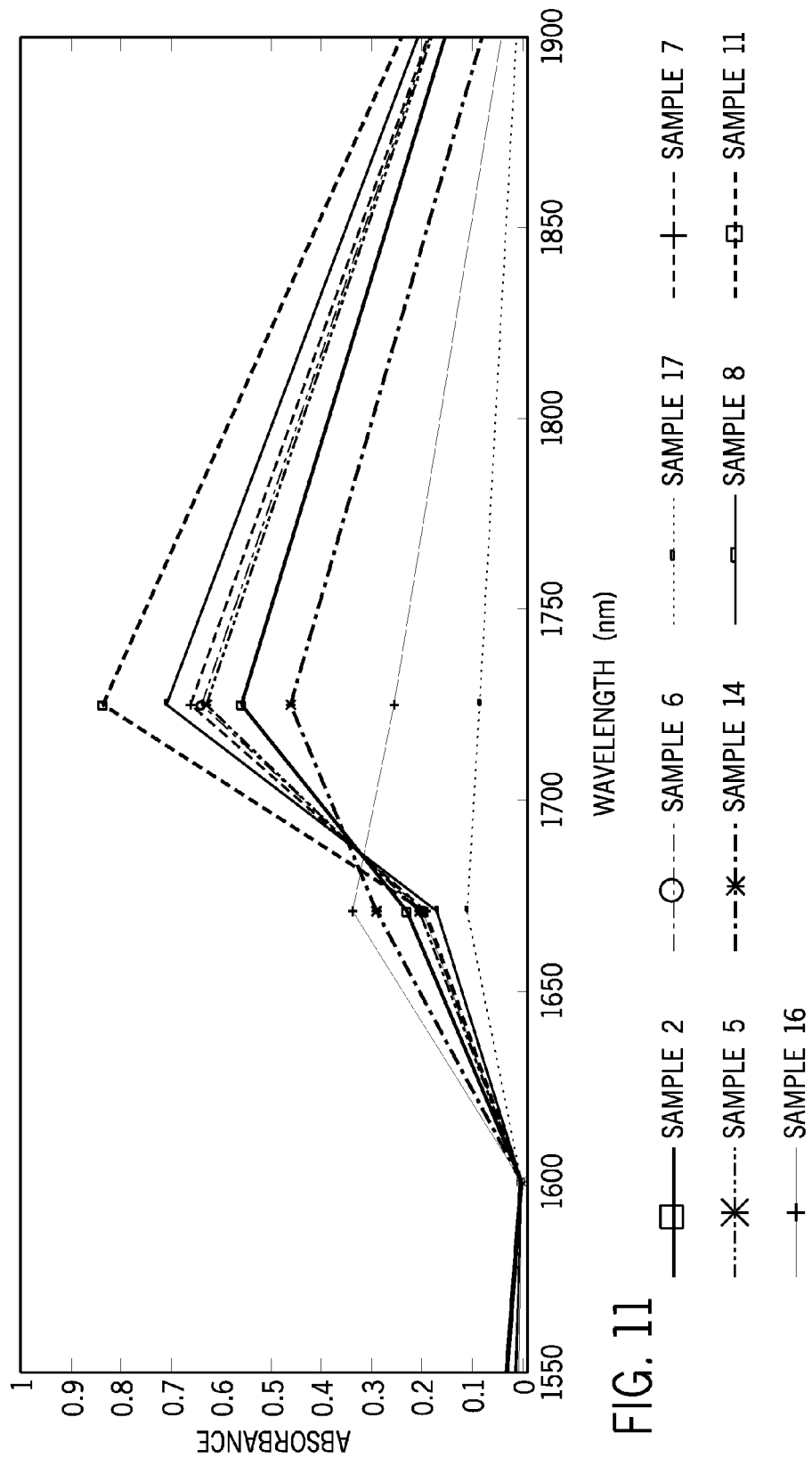
FIGS. 11 and 12 are graphs depicting optical densities of seventeen formation fluid samples measured at several wavelengths in accordance with one embodiment.
Figure 12:
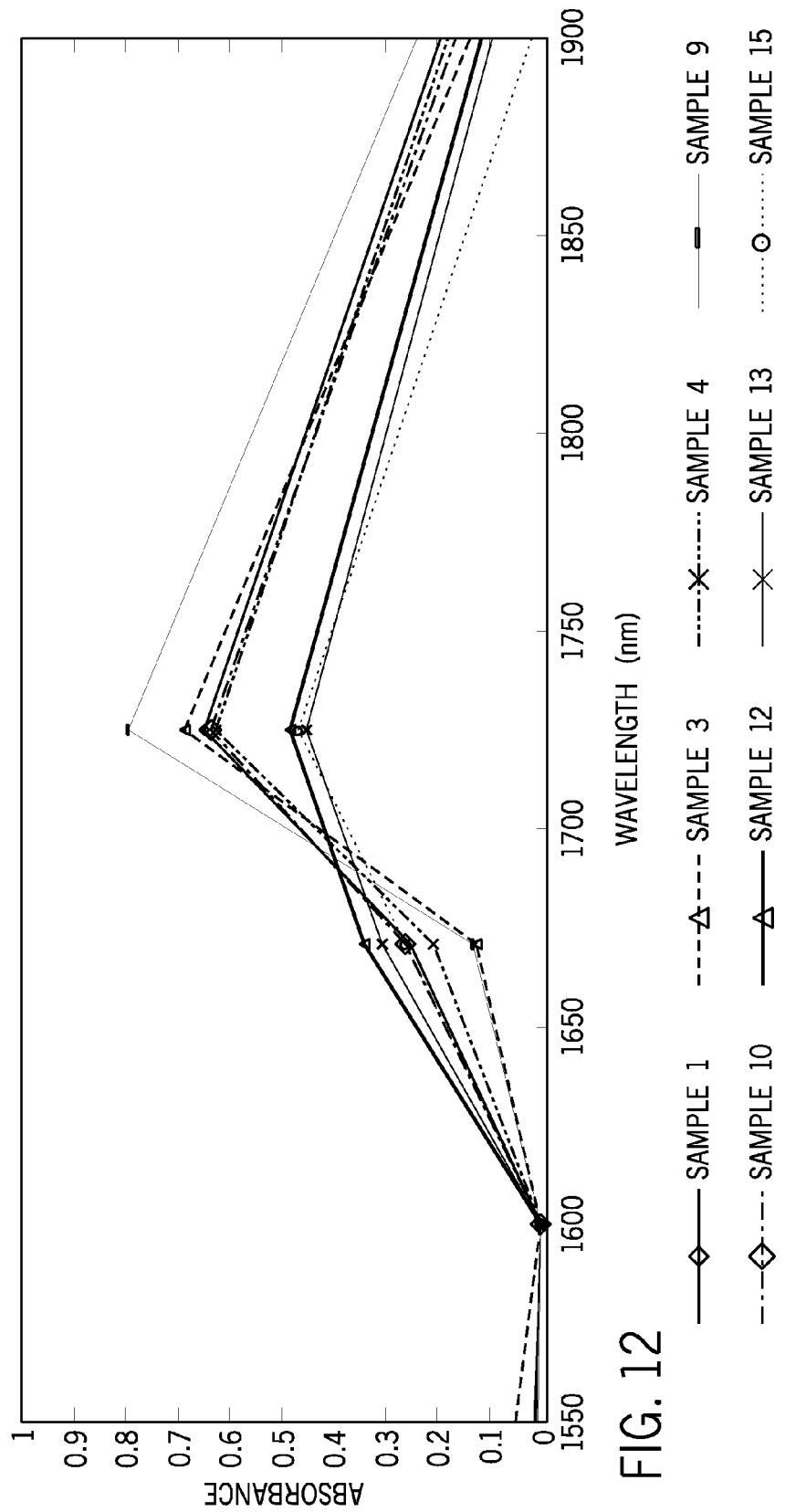

By way of further example, FIGS. 11 and 12 exhibit optical spectra of seventeen reservoir fluid samples measured with a downhole spectrometer, such as spectrometer 104. More particularly, absorbance (i.e., optical densities) of the reservoir fluid samples at three, near-infrared channels (1600 nm, 1671 nm, and 1725 nm) around hydrocarbon peaks are shown in these two figures. The optical densities for the seventeen samples are divided between FIGS. 11 and 12 for clarity so that the represented data can be more easily read. The fluid types of the seventeen samples were determined by laboratory PVT analysis and are shown in the following table:

TABLE 1

Fluid classification results from laboratory PVT analysis and optical density ratios

| Sample | PVT Report | OD Ratio | Fluid ID from OD ratio |
|---|---|---|---|
| Sample #1 | Oil | 0.39 | Oil |
| Sample #2 | Oil | 0.41 | Oil |
| Sample #3 | Oil | 0.18 | Oil |
| Sample #4 | Oil | 0.32 | Oil |
| Sample #5 | Oil | 0.32 | Oil |
| Sample #6 | Oil | 0.31 | Oil |
| Sample #7 | Oil | 0.28 | Oil |
| Sample #8 | Oil | 0.23 | Oil |
| Sample #9 | Oil | 0.16 | Oil |
| Sample #10 | Oil | 0.40 | Oil |
| Sample #11 | Oil | 0.23 | Oil |
| Sample #12 | Gas Condensate | 0.70 | Gas Condensate |
| Sample #13 | Gas Condensate | 0.67 | Gas Condensate |
| Sample #14 | Gas Condensate | 0.63 | Gas Condensate |
| Sample #15 | Gas Condensate | 0.56 | Oil/Gas Condensate |
| Sample #16 | Wet Gas | 1.4 | Gas Condensate/Wet Gas |
| Sample #17 | Gas Condensate | 1.2 | Gas Condensate/Wet Gas |
| Methane | | ~2.1 | Gas |
| A Dead Oil | | 0.1~0.15 | Oil |

This table also summarizes the optical density ratios of the samples and the identification of the fluid type based on the optical density ratio as described above. As shown in Table 1, the fluid typing obtained using the optical density ratio is generally consistent with the fluid type determined using laboratory results (PVT analysis).

Figure 13:
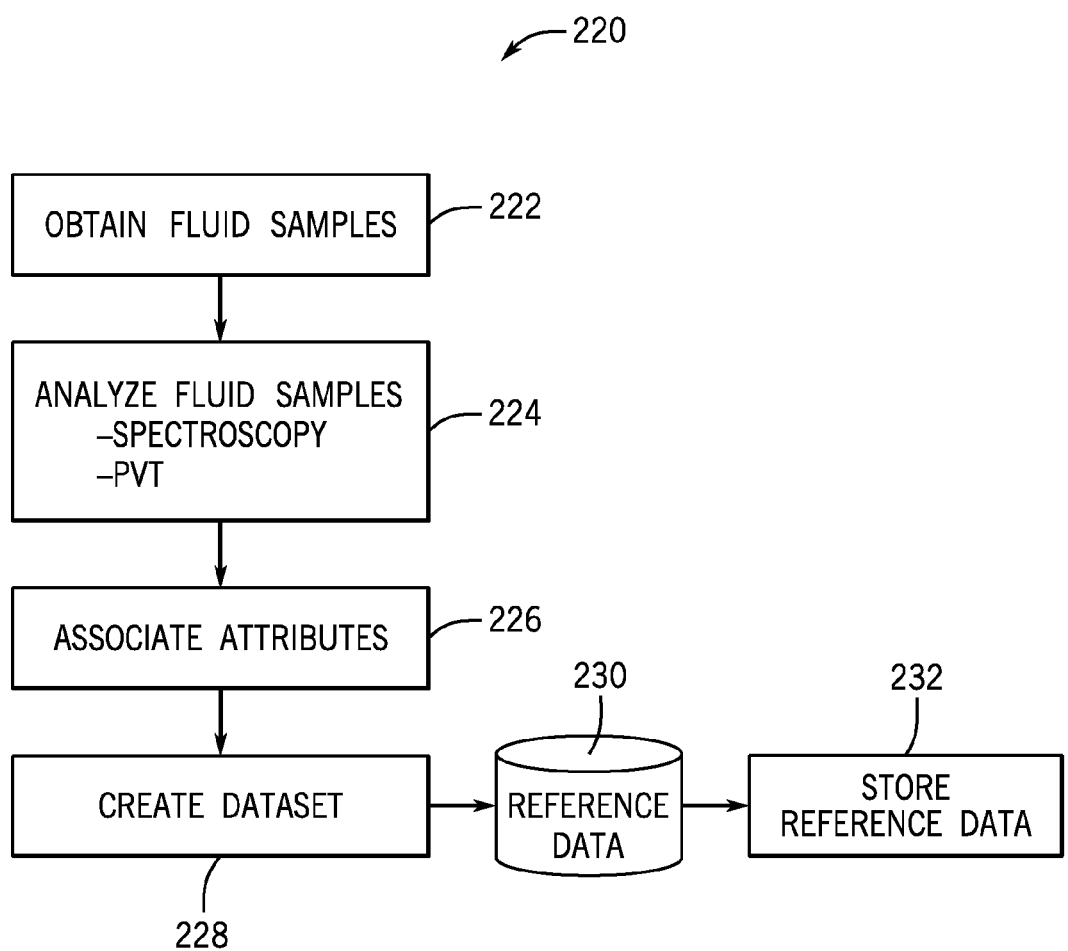
FIG. 13 is a flow chart for creating a reference data set of correlations between optical properties and other attributes of sample fluids in accordance with one embodiment.

As noted above, characterization of fluid attributes in some embodiments may rely on standardized reference data collected from known fluids. One example of a process of generating such reference data is generally represented by a flow chart 220 in FIG. 13, but the reference data could be generated in any other suitable ways. In FIG. 13, fluid samples are obtained (block 222) and then analyzed (block 224). In one embodiment, the fluid samples are obtained downhole in a well with a fluid sampling tool and then brought to the surface for analysis. Such analysis may include PVT analysis to determine the certain attributes of the fluid samples (e.g., fluid type) and spectroscopy to determine other attributes (e.g., optical properties, such as absorbance or optical density ratios). In other instances, one can recombine fluids based on known PVT reports and acquire optical densities of the recombined fluids (e.g., in a laboratory). In different embodiments, other forms of analysis may also or instead be used to determine attributes of the fluid samples. As represented by block 226, the attributes determined through various analyses are associated with one another to create (block 228) a dataset of reference data 230 that can be used to facilitate real-time characterization of unknown fluids sampled by a downhole tool without removing the unknown fluids to the surface for analysis. The reference data 230 may be provided in any suitable form, such as data representing one or more look-up tables, charts, graphs, or the like. Additionally, the reference data 230 may be stored (block 232) in any suitable memory, such as a memory device of the fluid sampling tool 62 or of some other downhole tool.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:

1. A method comprising:
    measuring absorbance by a sample of a formation fluid at a plurality of wavelengths of electromagnetic radiation with a spectrometer; and
    distinguishing between multiple fluid types to identify a fluid type of the sample most likely to match an actual fluid type of the sample based on the measured absorbance at two or more wavelengths of the plurality of wavelengths,
    wherein distinguishing between the multiple fluid types comprises:
        comparing the measured absorbance at a first wavelength of the two or more wavelengths to the measured absorbance at a second wavelength of the two or more wavelengths,
        calculating an absorbance ratio based on the measured absorbance at the first wavelength and the measured absorbance at the second wavelength, and comparing the calculated absorbance ratio to a set of benchmark data of calculated absorbance ratios for different types of formation fluids to identify the most likely fluid type of the sample.

2. The method of claim 1, comprising adjusting both the measured absorbance at the first wavelength and the measured absorbance at the second wavelength with a spectral offset before calculating the absorbance ratio.

3. The method of claim 2, wherein the spectral offset is determined from measured absorbance by the sample at a third wavelength of the plurality of wavelengths.

4. The method of claim 1, comprising determining a probability that the actual fluid type of the sample is the identified, most likely fluid type of the sample.

5. The method of claim 4, comprising determining an additional probability that the actual fluid type of the sample is instead another fluid type of the multiple fluid types different from the identified, most likely fluid type.

6. The method of claim 1, comprising collecting the sample of the formation fluid from a well using a downhole tool.

7. The method of claim 6, wherein measuring absorbance by the sample of the formation fluid at the plurality of wavelengths of electromagnetic radiation with the spectrometer and distinguishing between the multiple fluid types to identify the most likely fluid type of the sample based on the measured absorbance at the two or more wavelengths of the plurality of wavelengths are performed in the well by the downhole tool.

8. A method comprising:
irradiating a formation fluid with light having at least a first wavelength and a second wavelength;
detecting a portion of the light that is transmitted through the formation fluid;
calculating a first optical density of the formation fluid with respect to the first wavelength of light and a second optical density of the formation fluid with respect to the second wavelength of light;
deriving an optical density ratio from the first optical density and the second optical density; and
characterizing a physical attribute of the formation fluid based on the optical density ratio;
wherein characterizing the physical attribute of the formation fluid based on the optical density ratio includes empirically correlating the optical density ratio to the physical attribute of the formation fluid through comparison of the optical density ratio to a database of optical density ratios and associated physical attributes for previously analyzed, known fluid samples.

9. The method of claim 8, comprising storing the database of optical density ratios and associated physical attributes for previously analyzed, known fluid samples in a memory device of a downhole tool to enable the downhole tool to perform the comparison of the optical density ratio to the database while within a well.

10. The method of claim 8, comprising creating the database of optical density ratios and associated physical attributes from data derived through Pressure-Volume-Temperature analysis of the previously analyzed, known fluid samples.

11. The method of claim 8, wherein characterizing a physical attribute of the formation fluid includes characterizing a fluid type of the formation fluid.

12. An apparatus comprising:
a downhole sampling tool including an intake configured to receive a formation fluid within the downhole sampling tool and a downhole fluid analysis module having a spectrometer and configured to enable measurement of optical densities of the received formation fluid at different wavelengths of electromagnetic radiation; and
a controller operable to characterize a fluid type of the received formation fluid using the optical densities of the received formation fluid;
wherein the controller operates to characterize the fluid type of the received formation fluid by calculating an optical density ratio based on two of the different wavelengths and comparing the calculated optical density ratio to a database, encoded in memory of the controller, of associations between optical density ratios and types of formation fluids.

13. The apparatus of claim 12, wherein the controller is operable to characterize the fluid type of the received formation fluid as at least one of a dry gas, a wet gas, a retrograde gas, or an oil.

14. The apparatus of claim 12, wherein a detector of the spectrometer is configured to detect near-infrared wavelengths and the controller is operable to determine the fluid type of the received formation fluid using optical densities of the received formation fluid at the near-infrared wavelengths.

15. The apparatus of claim 12, wherein the controller is provided within the downhole sampling tool.

* * * * *